US012258502B2

(12) United States Patent
Olson (10) Patent No.: US 12,258,502 B2
(45) Date of Patent: Mar. 25, 2025

(54) ANTIMICROBIAL METALLIZED THIN FILMS FOR REFURBISHING COMMUNAL CONTACT SURFACES

(71) Applicant: Flex Ltd., Singapore (SG)

(72) Inventor: Bruce D. Olson, Northfield, MN (US)

(73) Assignee: Flex Ltd., Singapore (SG)

( * ) Notice: Subject to any disclaimer, the term of this patent is extended or adjusted under 35 U.S.C. 154(b) by 0 days.

(21) Appl. No.: 18/449,092

(22) Filed: Aug. 14, 2023

(65) Prior Publication Data

US 2023/0392048 A1    Dec. 7, 2023

Related U.S. Application Data

(62) Division of application No. 16/936,665, filed on Jul. 23, 2020, now abandoned.

(51) Int. Cl.
| | |
|---|---|
| *C09J 7/22* | (2018.01) |
| *A61L 2/238* | (2006.01) |
| *A61L 101/30* | (2006.01) |
| *B32B 7/12* | (2006.01) |
| *B32B 27/06* | (2006.01) |

(Continued)

(52) U.S. Cl.
CPC .............. *C09J 7/22* (2018.01); *A61L 2/238* (2013.01); *B32B 7/12* (2013.01); *B32B 27/06* (2013.01);

(Continued)

(58) Field of Classification Search
CPC ....... C09J 7/22; C09J 7/405; C09J 7/38; C09J 5/00; C09J 2400/163; C09J 2483/005;

(Continued)

(56) References Cited

U.S. PATENT DOCUMENTS

2008/0044458 A1   2/2008 MacDonald et al.
2010/0190004 A1*  7/2010 Gibbins ............... A61F 13/02
                                              428/343

(Continued)

OTHER PUBLICATIONS

Lewis, "The Hygienic Benefits of Antimicrobial Copper Alloy Surfaces in Healthcare Settings", 2009, International Copper Association (Year: 2009).*

(Continued)

*Primary Examiner* — Alicia J Weydemeyer
*Assistant Examiner* — Laura B Figg
(74) *Attorney, Agent, or Firm* — Sheridan Ross P.C.

(57) ABSTRACT

An antimicrobial metallized thin film is provided that can be quickly and easily attached to surfaces of objects. This film includes a polymer substrate onto which a metallized layer is formed. The metallized layer comprises an exposed antimicrobial metal physical contact surface. Ions from this physical contact surface destroy the viral coating and ribonucleic acid of contacting viruses rendering the viruses inactive and noninfectious. The film can be attached via an adhesive layer disposed between and in contact with the polymer substrate and the communal surface. This arrangement allows the film to economically refurbish communal surfaces with a film overlay rather than completely replacing communal surfaces with antimicrobial materials. The film mitigates the likelihood of viruses such as coronaviruses, noroviruses, rhinoviruses, and the like from spreading due to contact with the refurbished communal surfaces.

20 Claims, 7 Drawing Sheets

(51) Int. Cl.
  *B32B 37/12*    (2006.01)
  *B32B 38/00*    (2006.01)
  *C09J 5/00*     (2006.01)
  *C09J 7/38*     (2018.01)
  *C09J 7/40*     (2018.01)
  *C22C 9/04*     (2006.01)

(52) U.S. Cl.
  CPC .......... *B32B 37/12* (2013.01); *B32B 38/0004* (2013.01); *C09J 5/00* (2013.01); *C09J 7/38* (2018.01); *C09J 7/405* (2018.01); *C22C 9/04* (2013.01); *A61L 2101/30* (2020.08); *B32B 2255/10* (2013.01); *B32B 2255/205* (2013.01); *B32B 2405/00* (2013.01); *C09J 2400/163* (2013.01); *C09J 2483/005* (2013.01)

(58) Field of Classification Search
  CPC ....... A61L 2/238; A61L 2101/30; B32B 7/12; B32B 27/06; B32B 37/12; B32B 38/0004; B32B 2255/10; B32B 2255/205; B32B 2405/00; C22C 9/04
  See application file for complete search history.

(56) References Cited

U.S. PATENT DOCUMENTS

| | | | | |
|---|---|---|---|---|
| 2014/0370313 A1* | 12/2014 | Thomas | .............. | C23C 18/1893 205/159 |
| 2022/0025218 A1 | 1/2022 | Olson | | |

OTHER PUBLICATIONS

OED entry for 'ink' (Year: 2022).
Van Doremalen et al., "Aerosol and Surface Stability of SARS-CoV-2 as Compared with SARS-CoV-1," The New England Journal of Medicine, Mar. 2020, retrieved from https://www.nejm.org/doi/10.1056/NEJMc2004973, 5 pages.
Van Doremalen et al., Supplementary Appendix, to "Aerosol and Surface Stability of SARS-CoV-2 as Compared with SARS-CoV-1," The New England Journal of Medicine, DOI: 10.1056/NEJMc2004973, 10 pages.
Warnes et al., "Human Coronavirus 229E Remains Infectious on Common Touch Surface Materials," mBio, Nov./Dec. 2015, vol. 6(6), e01697-15, 20 pages.
Warnes et al., "Inactivation of Norovirus on Dry Copper Alloy Surfaces," PLoS One, Sep. 2013, vol. 8(9), pp. e75017, 9 pages.
Zerbib et al., "Copper for the Prevention of Outbreaks of Health Care-Associated Infections in a Long-term Care Facility for Older Adults," JAMDA, 2020, vol. 21, pp. 68-71e1.
Official Action for U.S. Appl. No. 16/936,665, dated Mar. 2, 2022 6 pages, Restriction Requirement.
Official Action for U.S. Appl. No. 16/936,665, dated Oct. 3, 2022 13 pages.
Final Action for U.S. Appl. No. 16/936,665, dated Apr. 14, 2023 12 pages.

\* cited by examiner

| MATERIAL TYPE AND THICKNESSES | | | |
|---|---|---|---|
| | Adhesive Sheet | Non-Adhesive Sheet | Rigid Sheet |
| Antimicrobial Metal Plating Layer 116 | 2.0 µ to 5.0 µ | 2.0 µ to 10.0 µ | 2.0 µ to 30 µ |
| Pre-Metallization Layer 120 | 0.1 µ to 5.0 µ | 0.1 µ to 5.0 µ | 0.1 µ to 5.0 µ |
| Substrate Layer 108 | 25 µ to 75 µ | 25 µ to 75 µ | 200 µ + |
| Adhesive Layer 124 | 25 µ to 75 µ | N/A | OPTIONAL 25 µ + |

ANTIMICROBIAL METALLIZED THIN FILMS FOR REFURBISHING COMMUNAL CONTACT SURFACES

CROSS-REFERENCE TO RELATED APPLICATIONS

This application is a division of U.S. patent application Ser. No. 16/936,665, filed Jul. 23, 2020, the contents of which is hereby incorporated by reference herein in its entirety.

BACKGROUND

The present disclosure is generally directed to thin films, in particular, toward the thin films including an antimicrobial metallized contact surface layer.

Viruses have the ability to remain active on contact surfaces from a matter of minutes to as long as days or weeks. While a virus remains active on a surface the threat of infection through physical contact exists. For instance, coronaviruses like MERS, SARS, and COVID-19, noroviruses, and even the common cold, can spread quickly between people in society because of the amount of time the viruses likely survive on many of the ubiquitous surfaces in use today. These surfaces generally include hard plastics, glass, ceramics, and stainless steels.

Recent studies have found that copper surfaces, or surfaces made from alloys rich in copper, rapidly deactivate the ribonucleic acid ("RNA") of a virus breaking it into fragments. In some cases, this deactivation may render a virus inactive on a surface and prevent the spread of the virus. Additionally or alternatively, presenting deactivated segments may have the benefit of inducing an immune response in anyone who subsequently touches the surface.

Most communal contact surfaces, like those associated with tables, shelves, doors, handles, light switch covers, and other objects, are not made from copper or even alloys rich in copper. Copper and other antimicrobial metals (e.g., silver, cadmium, etc.) are expensive and replacing objects with these antimicrobial metals is infeasible at scale.

DETAILED DESCRIPTION

It is with respect to the above issues and other problems that the embodiments presented herein were contemplated. The problem at hand relates to the current pandemic of COVID-19 and also relates to the general health of the world's population in general. It appears that the coronaviruses MERS, SARS, COVID-19, noroviruses, and even viruses that cause the common cold, likely survive for extended periods of time on many of the ubiquitous surfaces in use today. These surfaces include various hard plastics, glass, ceramics, and stainless steel. Research on human coronavirus 229E, suggest that a copper surface, or alloys rich in copper, rapidly deactivates the viral RNA breaking it into fragments. This may have the added benefit of presenting deactivated segments capable of inducing an immune response to anyone who subsequently touches the surface.

Installing a copper or high-copper brass surface is expensive and time consuming. Embodiments of the present disclosure provide a solution to this issue. For instance, the present disclosure describes a thin polymer film onto which a thin layer of copper, alloys rich in copper, silver, cadmium, zinc, or other antimicrobial metal are deposited. The resultant product is an antimicrobial metallized thin film that is lightweight and flexible. In some embodiments, the metallized layer thickness may be configured thin enough, and adhered to a polymer (e.g., plastic, etc.) substrate, such that the risk of cuts are mitigated or completely eliminated. In one embodiment, the backside of the antimicrobial metallized thin film may have an adhesive (e.g., a pressure sensitive adhesive, a thermoplastic adhesive, etc.) and a release liner attached thereto. The antimicrobial metallized thin film may be cut to shape and, after peeling off the release liner, applied to a communal surface. As can be appreciated, such a product enables the rapid transition of a communal surface on which a virus (e.g., coronavirus, norovirus, rhinovirus, etc.) has an extended survivability of days to a communal surface that is capable of deactivating the virus in less than half an hour in droplet form and less than ten minutes when transferred by fingerprints. This structure of the antimicrobial metallized thin film described herein does not present issues with sharp edges (e.g., causing papercuts or the like) as would be the potential with copper and/or brass foils adhered to a surface.

In some embodiments, the material of the metallized layer of the antimicrobial metallized thin film may be selected from a number of suitable antimicrobial metals depending on application. For example, the metallized thin film may be selected from Unified Number System (UNS) C21000 and/or C22000, which has an advantage of being more corrosion resistant than pure copper while still exhibiting similar antiviral properties.

In some embodiments, an antimicrobial metallized thin film is provided comprising a polymer film upon which a thin layer of copper, or other antimicrobial metal (e.g., silver, zinc, cadmium, etc., can be plated. The antimicrobial metal (e.g., pure copper or a copper-rich alloy, etc.) may be deposited on a first side of the polymer film and then plated up to a desired thickness of five microns or less. This thickness may provide an adequate structure that is able to withstand daily use for a predetermined amount of time. Additionally or alternatively, this thickness may provide the most economical use of the antimicrobial metal (e.g., still being effective at deactivating viruses while lasting on the film indefinitely). In any event, the thickness of the metallized layer being five microns, or less, prevents the likelihood of cuts from a body part sliding along an edge of the metallized layer.

In one embodiment, a pressure sensitive adhesive or low temperature thermoplastic adhesive may be applied to the opposite side of the film with an optional release liner. In some embodiments, however, an adhesive layer may be added at the time of application and, as such, may not need to be a part of the antimicrobial metallized thin film. In other embodiments, the antimicrobial metallized thin film may adhere to a surface through static cling. In such embodiments an adhesive may not be required and the antimicrobial metallized thin film and attachment surface may be cleaned thoroughly and simply brought into contact with and pressed against the attachment surface producing a cohesive force between the opposite side of the film and the attachment surface. In any event, the antimicrobial metallized thin film products described herein may be used in roll or sheet form.

Recent studies have demonstrated that a pure copper or copper-rich brass (e.g., ≥90% Cu) metallized layer may provide increased deactivation of viruses over metallized layers having less than 90% copper composition. In some embodiments, the metallized layer of the antimicrobial metallized thin film may be made from a copper-rich brass, which is more corrosion resistant than pure copper.

It is an object the present disclosure to provide an economical antimicrobial metallized thin film that can be easily and rapidly deployed onto communal surfaces, thus greatly decreasing the transmission of human coronaviruses, noroviruses, rhinoviruses, and/or any other viruses from the communal surfaces. In some embodiments, the antimicrobial metallized thin film may comprise an adhesive layer (e.g., pressure sensitive adhesive, thermoplastic adhesive, etc.) that can be selectively releasable from most surfaces for either replacement or discontinuation. In one embodiment, the antimicrobial metallized thin film may be adhered to a cleaned surface via static cling (e.g., without the use of adhesives or an adhesive layer). As can be appreciated, the present disclosure provides a safe and cost-effective solution to the alternative of completely replacing communal surfaces with surfaces made from antimicrobial metals (e.g., silver, copper, or brass, zinc, cadmium, etc.). Completely replacing plates, tables, fixtures, and/or other communal surfaces with those made from antimicrobial metals would be prohibitively expensive and would also require significantly more time to deploy. It is with respect to the above issues and other problems that the embodiments of the antimicrobial metallized thin film were contemplated.

Figure 1A:
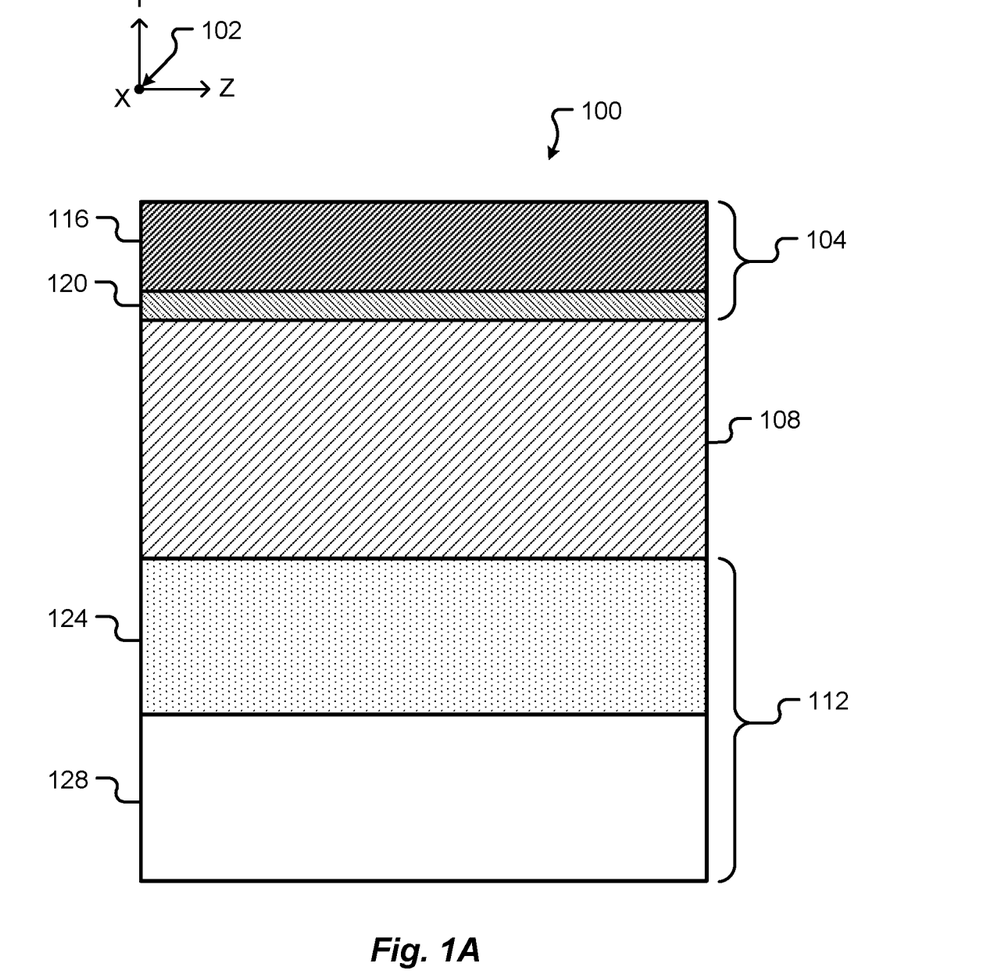
FIG. 1A shows a schematic section view of an antimicrobial metallized thin film in accordance with embodiments of the present disclosure.
Figure 1B:
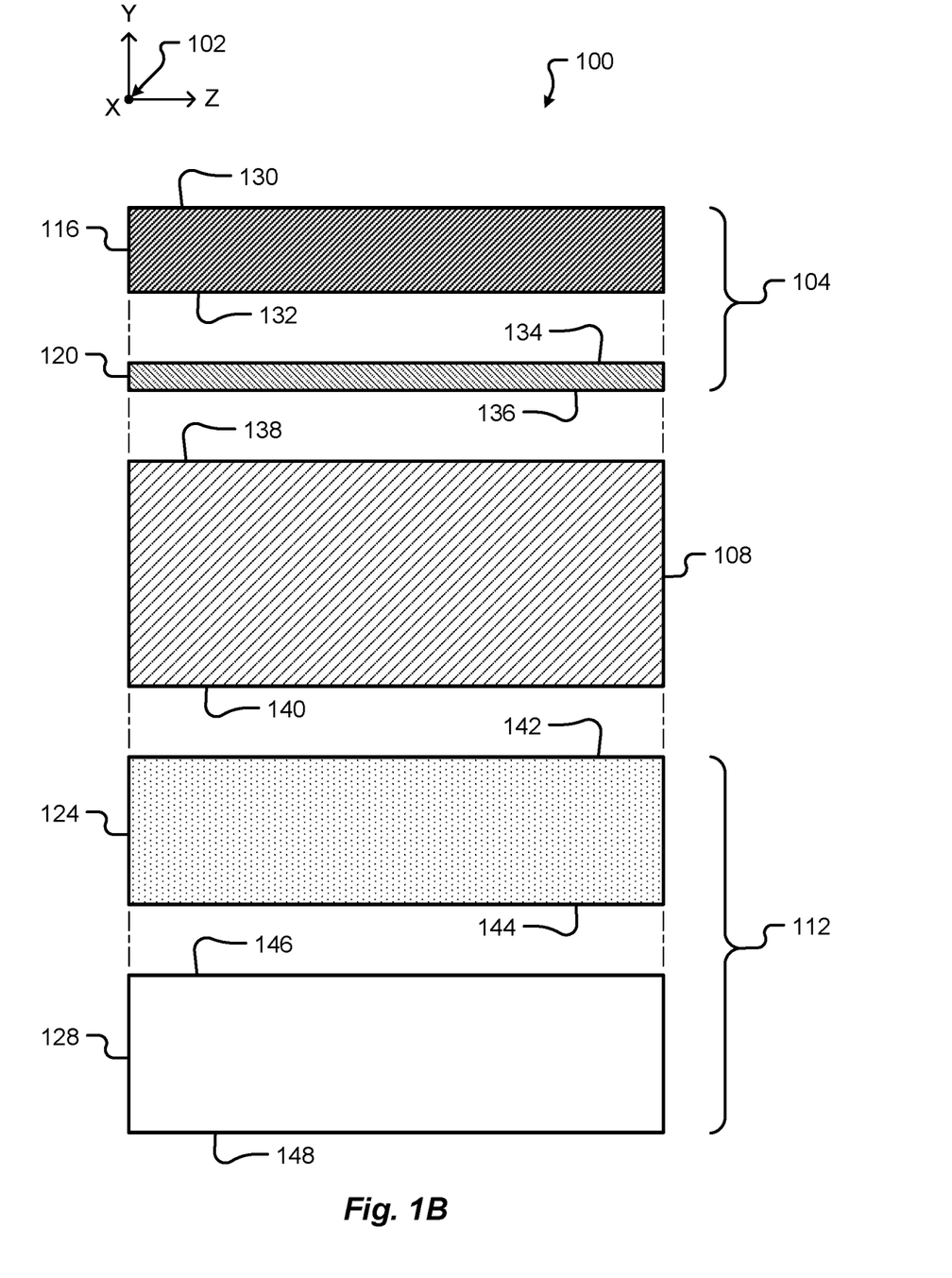
FIG. 1B shows an exploded section view of the antimicrobial metallized thin film of FIG. 1A in accordance with an embodiment of the present disclosure.

Referring now to FIGS. 1A-1B, schematic section views of an antimicrobial metallized thin film 100 are shown in accordance with embodiments of the present disclosure. In some embodiments, the antimicrobial metallized thin film 100 may at least comprise a substrate layer 108 onto which a metallized layer 104 having antimicrobial properties is formed. For instance, the metallized layer 104 may comprise a pre-metallization layer 120 and an antimicrobial metal plating layer 116. In some embodiments, the antimicrobial metallized thin film 100 may additionally comprise an attachment layer 112 formed on the substrate layer 108. The attachment layer 112 may comprise at least one of an adhesive layer 124 and a release liner 128. The various layers of the antimicrobial metallized thin film 100 may form a laminate in sheet or strip form. In one embodiment, the sheets or strips may be stored in stacks (e.g., similar to stacks of paper, etc.) or wrapped around a core (e.g., forming a roll of the film). In some cases, a roll of the antimicrobial metallized thin film 100 including the attachment layer 112 may serve as a type of tape that can be easily cut to length and then adhered to surfaces of an object.

The coordinate system 102, as shown in the figures, includes three-dimensions comprising an X-axis, a Y-axis, and a Z-axis. Additionally or alternatively, the coordinate system 102 may be used to define planes (e.g., the XY-plane, the XZ-plane, and the YZ-plane) of the antimicrobial metallized thin film 100. These planes may be disposed orthogonal, or at 90 degrees, to one another. While the origin of the coordinate system may be placed at any point on or near the components of the antimicrobial metallized thin film 100, for the purposes of description, the axes of the coordinate system 102 are always disposed along the same directions from figure to figure. In some embodiments, reference may be made to dimensions, angles, directions, relative positions, and/or movements associated with one or more components of the antimicrobial metallized thin film 100 with respect to the coordinate system 102.

The substrate layer 108 may comprise a polymeric film material. For example, the substrate layer 108 may be made from polyethylene, polypropylene, polyethylene terephthalate ("PET"), polyimide, vinyl, copolymers, other synthetic polymers, natural polymeric materials, etc., and/or combinations thereof. The substrate layer 108 may serve as the polymeric film to which the metallized layer 104 and/or the attachment layer 112 is formed. The substrate layer 108 may be arranged as a planar film. As shown in FIG. 1B, the substrate layer 108 may comprise a first side 138 and a second side 140 disposed opposite to the first side 138. The distance between the first side 138 and the second side 140 may define a thickness of the substrate layer 108. In some embodiments, the substrate layer 108 may comprise a woven or a nonwoven textile material.

The substrate layer thickness may be selected based on a particular material type and/or application of the antimicrobial metallized thin film 100. By way of example, the substrate layer thickness may be measured in a range of 25μ to 75μ when used as an adhesive or non-adhesive thin film sheet. In one embodiment, the substrate layer thickness may be measured in a range of 6μ to 25μ, or more. For instance, a substrate layer 108 made from PET or other polymeric material may allow for as small as a 6.0μ thickness. As can be appreciated, a 6.0μ thickness substrate layer may provide a very thin and flexible antimicrobial metallized thin film 100. In some embodiments, the thickness of the substrate layer 108 may be set to approximately 12μ to offer greater handleability and workability compared to the 6.0μ thickness substrate layer 108. In any event, these types of sheets may be arranged as an overlay that is capable of covering one or more communal surfaces. An example of a communal surface may correspond to a stainless steel or plastic tabletop. In this example, the communal surface (e.g., a surface of the tabletop) may be refurbished by attaching (e.g., adhering, pasting, clinging, etc.) the antimicrobial metallized thin film 100 in the form of a thin film sheet to the tabletop such that the physical contact surface 130 of the antimicrobial metal plating layer 116 is exposed. By covering the stainless steel or plastic surface of the tabletop, the refurbished physical contact surface 130 of the antimicrobial metal plating layer 116 provides a virucidal interface and contact surface that inactivates viruses and mitigates the spread of infection. In some embodiments, the substrate layer thickness may be greater than 75µ. In the event that a surface is to be replaced with a rigid, or semi-rigid, sheet of material, the substrate layer thickness may be greater than 200µ. Among other things, a rigid sheet may be used to refurbish, heavy-duty work surfaces (e.g., work benches, laboratory tables, etc.), heavy traffic surfaces (e.g., handrails, light switches, etc.) and/or other any other surface of objects where the antimicrobial metallized thin film 100 may remain attached on a semi-permanent (e.g., non-temporary) basis.

In some embodiments, the substrate layer 108 may provide an electrical insulation layer between the metallized layer 104 and the surface to be refurbished. The substrate layer 108 may be made from an electrically insulative polymeric material. Additionally or alternatively, the substrate layer thickness may be sized to prevent, or minimize, an electrical path between the metallized layer 104 and the surface to be refurbished. This insulation may prevent galvanic corrosion between dissimilar metals of the metallized layer 104 and the surface to be refurbished. In some embodiments, the metallized layer 104 may be intentionally electrically grounded to the surface to be refurbished, an object, a grounding pad, etc. Among other things, this electrical grounding may prevent the buildup of static electricity and/or the like between the antimicrobial metallized thin film 100 and other objects/surfaces.

The antimicrobial metallized thin film 100 may comprise a metallized layer 104 formed on the first side 138 of the substrate layer 108. In some embodiments, a pre-metallization layer 120 may be required to be formed on the first side 138 of the substrate layer 108 to plate the substrate layer 108 with an antimicrobial metal plating layer 116. The pre-metallization layer 120 may correspond to an electroless plated or vapor-deposited layer of metal. For instance, the pre-metallization layer 120 may correspond to an electroless copper plating layer, an electroless nickel plating layer, and/or some other electroless metal plating of the first side 138 of the substrate layer 108. In some embodiments, the pre-metallization layer 120 may be a vapor-deposited copper, nickel, or some other metal plating to which the antimicrobial metal plating layer 116 may be formed via plating. In one embodiment, the pre-metallization layer 120 may be printed onto the first side 138 of the substrate layer 108. For example, the pre-metallization layer 120 may be printed using one or more metallic printing inks such as silver, copper, graphite, carbon, etc., and/or combinations thereof. A printed pre-metallization layer 120 (e.g., using the printing inks, etc.) may be electroplated and provide further benefits to producing the antimicrobial metallized thin film 100. For example, in the event that a woven or nonwoven textile is selected as the substrate layer 108, the printing of the pre-metallization layer 120 on the first side 138 of the substrate layer 108 may allow for variations in surface treatments, textures, gaps, and/or other inconsistencies. In any event, the pre-metallization layer 120 serves as a surface treatment of the first side 138 of the substrate layer 108 that is capable of accepting the plating of the antimicrobial metal plating layer 116. The pre-metallization layer 120 may be made of the same, or similar, metal as the antimicrobial metal plating layer 116. In one embodiment, the pre-metallization layer 120 may be made of a different, or dissimilar, metal from the antimicrobial metal plating layer 116. Utilizing the same metal (e.g., a metal having a high-percentage of copper, silver, cadmium, zinc, etc.) for both the antimicrobial metal plating layer 116 and the pre-metallization layer 120 may prevent corrosion, provide enhanced plating properties, and/or provide greater virucidal properties.

In some embodiments, the pre-metallization layer 120 may be deposited on the first side 138 of the substrate layer 108 at a thickness measured anywhere between and including 0.05µ to 0.5µ. In one embodiment, the pre-metallization layer 120 may be formed on the first side 138 of the substrate layer 108 at a thickness measured anywhere between and including 0.1µ to 0.2µ. The reduced thickness of the pre-metallization layer 120 may still allow plating of the antimicrobial metal plating layer 116 without requiring further time and/or expense required in depositing material thicker than 0.1µ to 0.2µ.

The antimicrobial metal plating layer 116 may be plated at a thickness anywhere between and including 1.0µ to 5.0µ. In one embodiment, the antimicrobial metal plating layer 116 may be formed on the plating side 134 of the antimicrobial metal plating layer 116 extending a thickness anywhere between and including 2.0µ to 5.0µ. A benefit of maintaining the overall thickness of the antimicrobial metal plating layer 116 at a dimension less than or equal to approximately 5.0µ may include preventing accidental cuts of body parts contacting an edge of the antimicrobial metal plating layer 116 (e.g., an edge running along the physical contact surface 130 in the Z-axis direction or in the X-axis direction, etc.). While the thickness of the antimicrobial metal plating layer 116 may be increased above 5.0µ, the risk of a cut (e.g., a papercut type of cut) to a body part sliding along the edge of the antimicrobial metal plating layer 116 may correspondingly increase. The plating thickness range between, and including, 2.0µ and 5.0µ for the antimicrobial metal plating layer 116 may provide the most economical size range for the antimicrobial metal plating layer 116. At this thickness range, a sufficient amount of material is provided to inactivate contacting viruses, the material is resistant to wear, and the material provides the lowest risk of accidental cuts to body parts (e.g., fingers, hands, etc.).

Although described as including an antimicrobial metal plating layer 116 and a pre-metallization layer 120, it should be appreciated that the antimicrobial metal plating layer 116 may be formed directly on the first side 138 of the substrate layer 108 (e.g., without the pre-metallization layer 120, etc.) at suitable thickness via electroless plating and/or vapor-deposition. At least one advantage of using the pre-metallization layer 120 before adding the antimicrobial metal plating layer 116 at includes an inexpensive and quick plating operation compared to the timely and costly vapor-deposition of metal at thicknesses greater than 1.0µ.

The antimicrobial metal plating layer 116 may be made from a material that deactivates the RNA of contacting viruses. Examples of the material may include antimicrobial agents such as copper, silver, zinc, cadmium, and/or the like. As provided herein, the efficacy of these materials in inactivating viruses (e.g., coronaviruses, noroviruses, rhinoviruses, etc.) may depend on the composition of the material. For instance, the higher the percentage concentration of antimicrobial metal in the antimicrobial metal plating layer 116, the higher the efficacy of the antimicrobial metal plating layer 116 in deactivating viruses. When the antimicrobial metal plating layer 116 is a metal alloy, having a combination of two or more metals, the percentage of the antimicrobial metal, or metals, may be selected to meet a predetermined efficacy threshold. By way of example, brass may be selected as the material of the antimicrobial metal plating layer 116. Brass includes copper as the primary antimicrobial metal alloyed with one or more other metallic elements. In selecting an effective antimicrobial type of brass, the percentage of copper in the alloy is considered. Copper-rich brass may refer to any brass alloy having a composition of copper greater than or equal to 90%. Examples of these copper-rich brass alloys may include, but are in no way limited to UNS C21000 and/or UNS C22000. UNS C21000 brass may correspond to an alloy containing approximately 95% copper and 5% zinc. UNS C22000 brass may correspond to an alloy containing approximately 90% copper and 10% zinc. Each of these alloys are highly effective at deactivating the RNA of contacting viruses. Although the present disclosure describes the benefits of high-percentage copper materials, it should be appreciated that any antimicrobial material may be used at the same, or similar, percentages with equal, or substantially similar, efficacy. Copper-rich alloys or metals offer a benefit of high viral inactivity efficacy (e.g., virucidal properties, etc.) and good wear characteristics (e.g., mechanical and/or anticorrosive properties, etc.) at an economical cost.

In some embodiments, the antimicrobial metallized thin film 100 may include an attachment layer 112. The attachment layer 112 may serve as a protective film for the substrate layer 108 and/or the adhesive layer 124. In one embodiment, the antimicrobial metallized thin film 100 may attach to surfaces via static cling. In this case, the adhesive layer 124 may be excluded from the substrate layer 108 and the release liner 128 may be formed directly to the second side 140 of the substrate layer 108. Prior to attaching the antimicrobial metallized thin film 100 to a surface (e.g., a communal surface to be refurbished, etc.), the release liner 128 may be removed from the substrate layer 108 exposing the second side 140.

In some embodiments, the antimicrobial metallized thin film 100 may include an adhesive layer 124 formed on the second side 140 of the substrate layer 108. The adhesive layer 124 may include a second side facing surface 142 and an adhesive attachment surface 144 disposed opposite the second side facing surface 142 and offset an adhesive layer thickness. As shown in FIGS. 1A-1B, the thicknesses of the various layers 104, 108, 112 are shown extending along the Y-axis of the coordinate system 102. The adhesive layer 124 may be made from at least one of a pressure-sensitive adhesive material, a solvent-based adhesive material, and a thermoplastic adhesive material. Additionally or alternatively, while the adhesive layer 124 is shown in FIGS. 1A-1B as being formed on the second side 140 of the substrate layer 108, the adhesive layer 124 may be added between the second side 140 and a surface to be refurbished (e.g., as a paste, a fluid, a separate tape, or other adhesive material) allowing the substrate layer 108 to adhere to the surface to be refurbished.

The antimicrobial metallized thin film 100 may include a release liner 128 attached to the adhesive attachment surface 144 of the adhesive layer 124. The release liner 128 may provide a protective layer of material for the adhesive attachment surface 144 of the adhesive layer 124. In some cases, the release liner 128 may prevent the adhesive attachment surface 144 from sticking or adhering to unintended surfaces. When stored as stacks of sheets, the release liner 128 may provide a non-adhesive barrier between adjacently stacked antimicrobial metallized thin films 100. The release liner 128 may be formed or coated with at least one release agent or nonstick layer disposed on a surface thereof. Examples of the release agent or nonstick layer material may include, but are in no way limited to, PET resin, polypropylene resin, polysiloxane (e.g., silicone), etc., and/or combinations thereof. For example, the release liner 128 may have a silicone coating on the adhesive contact surface 146. When the release liner 128 is attached to the adhesive layer 124, the adhesive contact surface 146 contacts the adhesive attachment surface 144 of the adhesive layer 124. The silicone coating on the adhesive contact surface 146 may allow for easy release of the release liner 128 from the adhesive attachment surface 144 of the adhesive layer 124 by peeling. In some embodiments, the external surface 148 may also be coated with a nonstick layer such as silicone. The body of the release liner 128 may be made from paper, polymer, vinyl, and/or any other film that is capable of being selectively removed from the adhesive layer 124. Examples of release liner 128 body may include, but are in no way limited to, calendered paper, super-calendered paper, glassine, paper, polyester, plastic, etc., and/or combinations thereof.

Figure 2A:
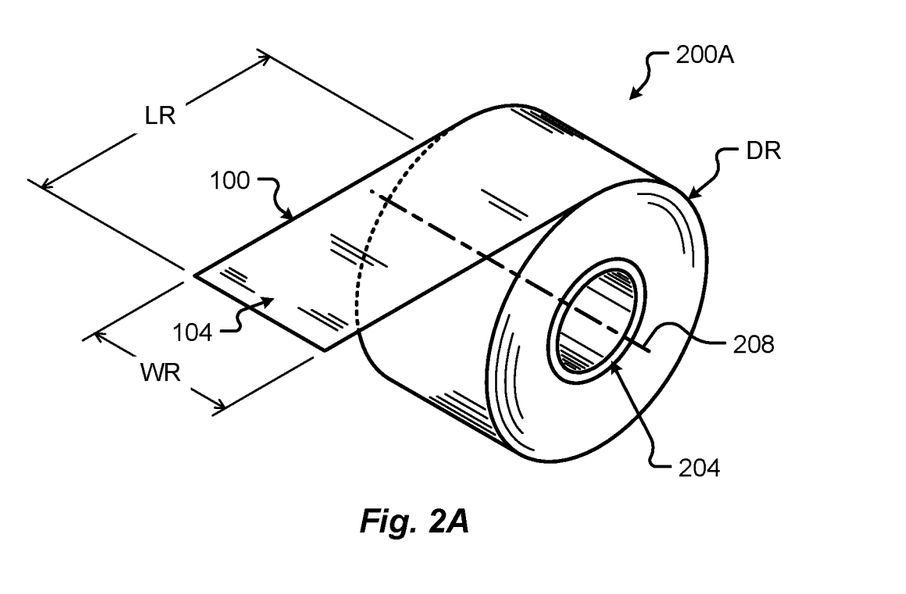
FIG. 2A shows a roll of antimicrobial metallized thin film in accordance with embodiments of the present disclosure.
Figure 2B:
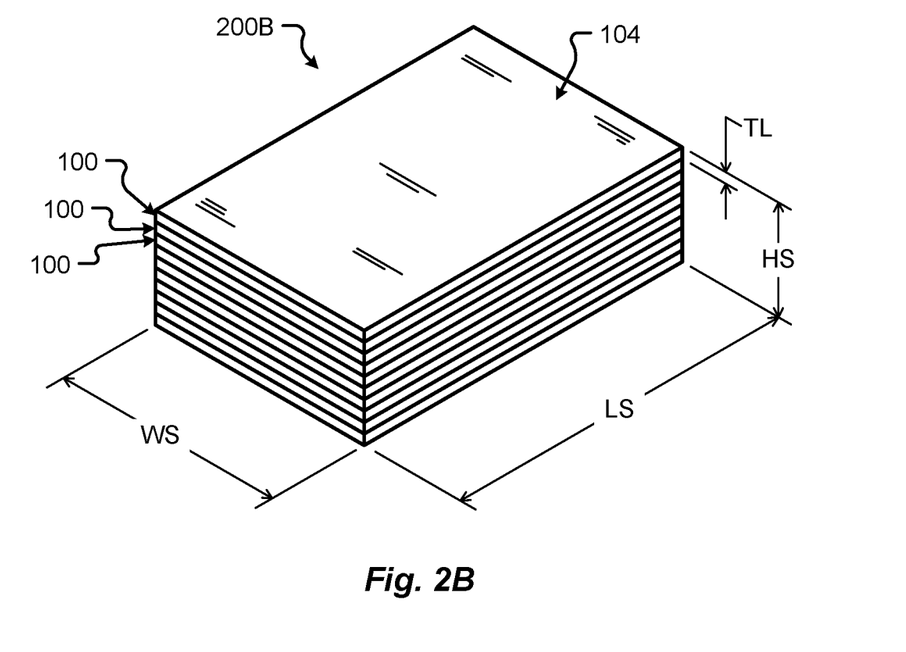
FIG. 2B shows a stack of antimicrobial metallized thin film sheets in accordance with embodiments of the present disclosure.

FIGS. 2A-2B show various packaging embodiments of the antimicrobial metallized thin film 100 described herein. The antimicrobial metallized thin film 100 may be packaged as rolls of material 200A and/or sheets of material 200B. In some embodiments, the sheets of material 200B may be wound onto a core 204 forming the roll of material 200A. The various layers of the antimicrobial metallized thin film 100 described in conjunction with FIGS. 1A-1B may be manufactured by a number of processes. In one embodiment, the antimicrobial metallized thin film 100 may be made by a converting machine that joins separate layers of material together in a continuous operation. As the antimicrobial metallized thin film 100 is produced, the film 100 may be wound onto cores 204 and cut to specific diameters or overall lengths. In some embodiments, the antimicrobial metallized thin film 100 may be made and stacked as individual sheets of material 200B, as shown in FIG. 2B. In any event, the sizes of the antimicrobial metallized thin film 100 may be selected to suit a particular application.

FIG. 2A shows a roll of material 200A including the antimicrobial metallized thin film 100 in accordance with embodiments of the present disclosure. The antimicrobial metallized thin film 100 is shown wound in a roll onto a core 204. The core 204 may correspond to a hollow cylindrical tube having a roll axis 208. The core 204 may be centerline symmetrical about the roll axis 208. The rolls of material 200A may be used to allow a refurbishing technician to pull a desired, or predetermined, roll-length, LR, of the antimicrobial metallized thin film 100 for cutting. The roll-length, LR, may be determined based on a size of the surface to be refurbished. The rolls of material 200A may be packaged in predetermined roll-widths, WR, and in predetermined roll-diameters, DR. The roll-width, WR, may define a width of the antimicrobial metallized thin film 100 and the roll-diameter, DR, may define a total length of the antimicrobial metallized thin film 100 wound onto the core 204.

As described herein, the antimicrobial metallized thin film 100 may be prepackaged in specific size configurations for various application types. For example, the antimicrobial metallized thin film 100 may be arranged as "narrow tapes" or as "wider sheets" on the rolls of material 200A. Examples of narrow tapes may include, but are in no way limited to, an antimicrobial metallized thin film 100 having a roll-width, WR, measuring in the range of 6.0 mm to 150 mm. The roll-diameters, DR, for these narrow tapes may range from 25.0 mm to 500 mm. In one embodiment, the roll-diameters, DR, the roll-widths, WR, and the dimension (e.g., inside diameter, width, etc.) of the cores 204 for the rolls of material 200A may be sized to fit a range of standard tape dispensers (e.g., desktop dispensers, handheld dispensers, industrial dispensers, etc.). Examples of wider sheets may include, but are in no way limited to, an antimicrobial metallized thin film 100 having a roll-width, WR, measuring in the range of 151 mm to 1,000 mm, or larger. The roll-diameters, DR, for these wider sheets may range from 501 mm to 1,200 mm, or larger. In one embodiment, the roll-diameters, DR, the roll-widths, WR, and the dimension (e.g., inside diameter, width, etc.) of the cores 204 for the rolls of material 200A may be sized to fit a range of roll dispensers (e.g., paper towel dispensers, industrial roll dispensers, taping machines, etc.). While the roll-widths, WR, of the rolls of material 200A may be set at specific predetermined sizes, a refurbishment technician may cut a desired length (e.g., the roll-length, LR) of material from the rolls of material 200A. Additionally or alternatively, the refurbishment technician may cut the roll-width, WR, of the rolls of material 200A to divide the overall roll-width, WR, by any amount desired. The rolls of material 200A allow continuous strips of the antimicrobial metallized thin film 100 to be adhered to a surface to be refurbished without any interruption in the exposed antimicrobial metal plating layer 116 along the length of the strip. Handrails and long narrow surfaces are an ideal application for the antimicrobial metallized thin films 100 that are arranged on rolls of material 200A.

The rolls of material 200A may include the attachment layer 112 disposed on the second side 140 of the substrate layer 108. As shown in FIG. 2A, the metallized layer 104 is shown on the outside of the rolls of material 200A, and the opposing surface of the antimicrobial metallized thin film 100 may include the attachment layer 112. The roll of material 200A may include the release liner 128 as part of the attachment layer 112, however, in some cases the release liner 128 may be omitted and the attachment layer 112 may only comprise the adhesive layer 124.

FIG. 2B shows a stack of antimicrobial metallized thin film 100 sheets of material 200B in accordance with embodiments of the present disclosure. In some embodiments, the antimicrobial metallized thin film 100 may be packaged as individual sheets of material 200B, where each sheet of the antimicrobial metallized thin film 100 has a defined sheet-width, WS, sheet-length, LS, and overall thickness, TL. The overall thickness, TL, of the antimicrobial metallized thin film 100 may correspond to the sum of the thicknesses of each layer making up the laminate structure of the antimicrobial metallized thin film 100. This overall thickness, TL, may depend on a particular material type and/or application for the antimicrobial metallized thin film 100. In general, the overall thickness, TL, of each antimicrobial metallized thin film 100 may range from 27µ to 300µ, or even thicker. Although not shown in FIG. 2A, the overall thickness, TL, applies to the antimicrobial metallized thin film 100 that are wrapped, or wound, in rolls of material 200A. The individual sheets of material 200B may be stacked one on top of another as shown in FIG. 2B. A stack of the sheets of material 200B may have an stack-height, HS. The stack-height, HS, may correspond to the sum of the overall thicknesses, TL, of each sheet in the stack.

Similar to the rolls of material 200A, the sheets of antimicrobial metallized thin film 100 may be prepackaged in specific size configurations suited to different application types. For example, the antimicrobial metallized thin film 100 sheets of material 200B may be arranged as "narrow strips" or as "wider sheets." Examples of narrow strips may include, but are in no way limited to, an antimicrobial metallized thin film 100 having a sheet-width, WS, measuring in the range of 100 mm to 150 mm. The sheet-length, LS, for the narrow strips may range from 100 mm to 1,200 mm, or larger. Examples of wider sheets may include, but are in no way limited to, an antimicrobial metallized thin film 100 having a sheet-width, WS, measuring in the range of 151 mm to 1,200 mm, or larger. The sheet-length, LS, for these wider sheets may range from 151 mm to 1,200 mm, or larger. The sheets of material 200B may be arranged in a stack having an overall stack-height, HS, that may be based on shipping container sizes, storage area sizes, sales quantities, packaging constraints, and/or the like. While the sheet-widths, WS, and the sheet-lengths, LS, of the sheets of material 200B may be set at specific predetermined sizes, a refurbishment technician may cut a desired length of material from the sheet-width, WS, and/or the sheet-length, LS, of the sheets of material 200B. Examples of applications for the sheets of material 200B may include, but are in no way limited to, refurbishment of tabletops, walls, shelves, trays, partitions, etc.

The sheets of material 200B may include the attachment layer 112 disposed on the second side 140 of the substrate layer 108. As shown in FIG. 2B, the metallized layer 104 is shown on the top surface of each sheet of the sheets of material 200B and the opposing surface of the antimicrobial metallized thin film 100 of each sheet may include the attachment layer 112. Each sheet of the sheets of material 200B may include the release liner 128 as part of the attachment layer 112, however, in some cases the release liner 128 may be omitted and the attachment layer 112 may only comprise the adhesive layer 124.

Figure 3A:
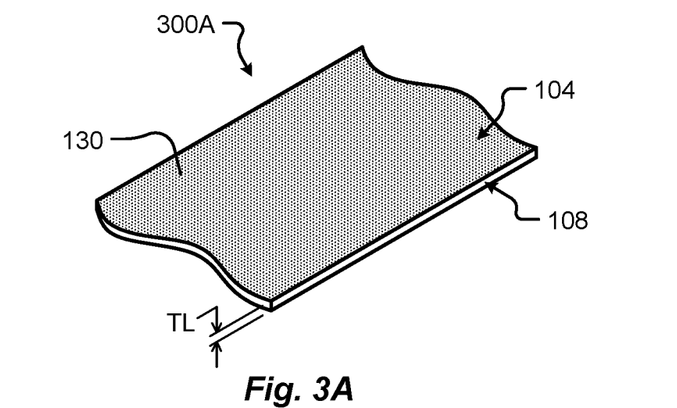
FIG. 3A shows a perspective detail view of a portion of the antimicrobial metallized thin film having a first plating arrangement in accordance with embodiments of the present disclosure.
Figure 3B:
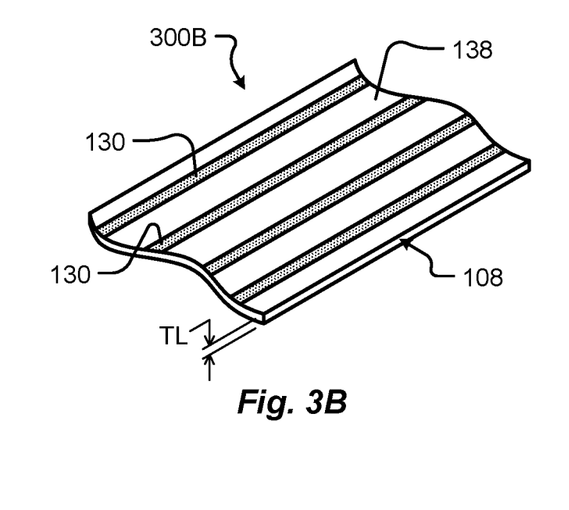
FIG. 3B shows a perspective detail view of a portion of the antimicrobial metallized thin film having a second plating arrangement in accordance with embodiments of the present disclosure.
Figure 3C:
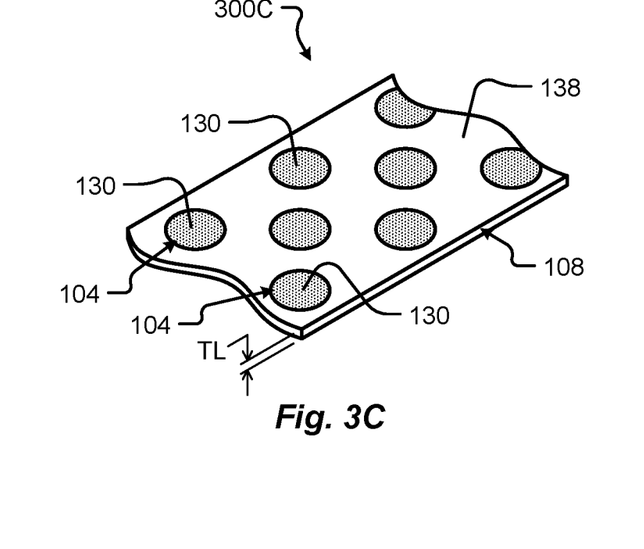
FIG. 3C shows a perspective detail view of a portion of the antimicrobial metallized thin film having a third plating arrangement in accordance with embodiments of the present disclosure.

Referring now to FIGS. 3A-3C, various perspective detail views of a portion of the antimicrobial metallized thin film 100 are shown in accordance with embodiments of the present disclosure. In some embodiments, the metallized layer 104 may cover an entirety of the first side 138 of the substrate layer 108 or only specific areas of the first side 138 of the substrate layer 108. When a reduced area (e.g., less than the entirety, etc.) of the first side 138 of the substrate layer 108 are covered by the metallized layer 104, the distance between each covered area having the virucidal physical contact surface 130 may depend on a number of factors. These factors may include, but are in no way limited to, deactivation efficacy and range of the material selected for the antimicrobial metal plating layer 116, a virus size, desired geometry, etc.

In FIG. 3A, a perspective detail view of a portion of the antimicrobial metallized thin film having a first plating arrangement 300A for the antimicrobial metal plating layer 116 is shown in accordance with embodiments of the present disclosure. The antimicrobial metal plating layer 116 shown in FIG. 3A shows the metallized layer 104, and antimicrobial metal plating layer 116 having the physical contact surface 130, covering a majority, if not an entirety, of the substrate layer 108. In this first plating arrangement 300A, the metallized layer 104 may remain exposed and uncovered (e.g., by any other film, layer, etc.) along the length and/or width of the substrate layer 108. Among other things, the first plating arrangement 300A provides a continuous surface area of antimicrobial metal for the physical contact surface 130 that deactivates the RNA of contacting viruses.

FIG. 3B shows a perspective detail view of a portion of the antimicrobial metallized thin film having a second plating arrangement 300B in accordance with embodiments of the present disclosure. In FIG. 3B, the metallized layer 104 is noncontinuous, or separated by distances, between virucidal physical contact surfaces 130 disposed on the substrate side 136 of the substrate layer 108. The separation distance between the physical contact surfaces 130 may correspond to an average droplet size that is capable of carrying a virus. In some embodiments, the separation distance between the physical contact surfaces 130 may correspond to a dimension that is less than an average droplet size that is capable of carrying a virus. Additionally or alternatively, the physical contact surface 130 may be similarly sized, sized smaller, or sized larger than the average droplet size that is capable of carrying a virus. Example droplet sizes may range from about 3μ to 120μ. In some embodiments, as long as a portion of the physical contact surface 130 of the antimicrobial metal plating layer 116 contacts a droplet having a virus, the ions from the physical contact surface 130 (e.g., from the antimicrobial metal plating layer 116) can destroy the viral coating and RNA of the virus in the droplet rendering the virus inactive and noninfectious. In FIG. 3B, the physical contact surface 130 are shown as strips of antimicrobial metal plating layer 116 that extend along a length or a width of the antimicrobial metallized thin film 100.

FIG. 3C shows a perspective detail view of a portion of the antimicrobial metallized thin film having a third plating arrangement 300C in accordance with embodiments of the present disclosure. In FIG. 3C, the physical contact surface 130 are shown as enclosed areas of antimicrobial metal plating layer 116 that are distributed in a pattern along the length and/or width of the antimicrobial metallized thin film 100. Although shown as circular, or elliptical, dots disposed on the substrate layer 108, the physical contact surfaces 130 may comprise any shape, or combination of shapes with a defined area. Similar to the physical contact surfaces 130 shown and described in conjunction with FIG. 3B, the physical contact surfaces 130 of FIG. 3C may be separated by one or more distances. For example, the virucidal physical contact surfaces 130 may be separated from one another in a width dimension and in a length dimension. The separation distances between the physical contact surfaces 130 in FIG. 3C may be related to an average droplet size that is capable of carrying a virus. In some embodiments, the separation distance between the physical contact surfaces 130 may correspond to a dimension that is less than an average droplet size that is capable of carrying a virus. The physical contact surfaces 130 of the third plating arrangement 300C may be of any size that fit on the substrate layer 108. Example sizes of the physical contact surface 130 in the third plating arrangement 300C may include, but are in no way limited to, any diameter from 25μ to 12,000μ, or even larger.

Figure 4:
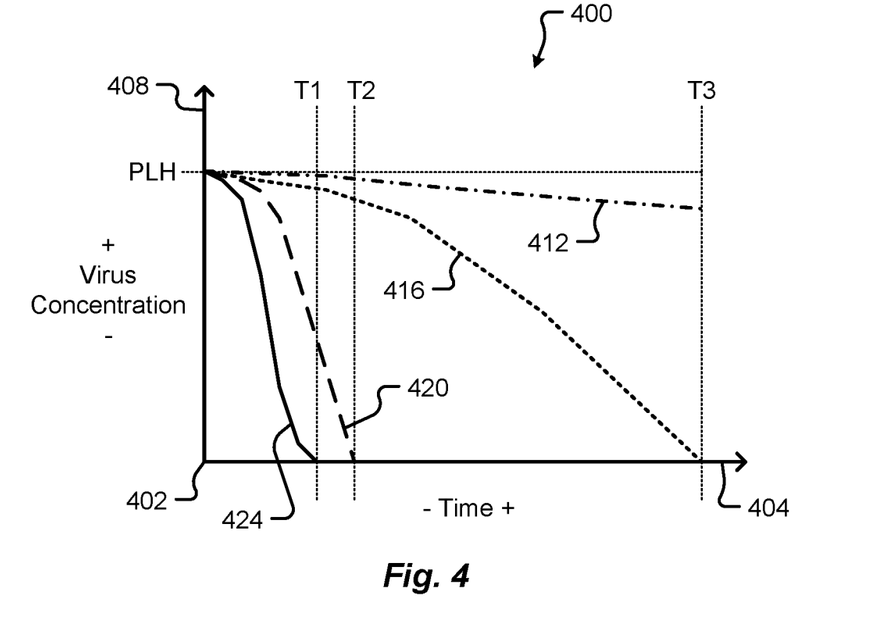
FIG. 4 shows a chart of comparative virus decay rates associated with different surface materials.

FIG. 4 shows a chart of surface material decay rate 400 for various surface materials in accordance with embodiments of the present disclosure. The chart of surface material decay rate 400 includes the deactivation time along the horizontal axis 404 increasing from the origin 402 to the right-hand side of the chart 400 and the virus concentration along the vertical axis 408 increasing moving away from the origin 402. In the chart 400, a droplet (e.g., of fluid, etc.) containing a known quantity, PLH, of active virus units for a virus, such as COVID-19, etc., is deposited on each of four different surface materials 412, 416, 420, 424. The known quantity, PLH, of active virus units shown on the vertical axis 408 may be measured in plaque forming units ("PFU"). At the origin, the number of active virus units may be zero. The time shown on the horizontal axis 404 may be measured in minutes.

The first material may correspond to a stainless steel material 412. Due to stainless steel's anticorrosive properties, this metal alloy is used in a number of surfaces in hospitals, laboratories, cleanrooms, and other sterilized environments. However, as can be observed on the chart of surface material decay rate 400, the number of active virus units remaining on the surface at a final test time, T3, is still close to the known quantity, PLH, of active virus units initially deposited on the stainless steel material 412 surface. In some embodiments, the final test time, T3, may correspond to 120 minutes, or two hours. As can be appreciated, the stainless steel material 412 fails to deactivate the virus in contact with the surface and, as such, the virus remains active on the surface for a long period of time.

Using an antimicrobial metal, such as a 70% copper material 416, produces a highly increased deactivation curve. For instance, while the number of active virus units at the first test time, T1, and the second test time, T2, remain close to the known quantity, PLH, of active virus units initially deposited on the 70% copper material 416 surface, at the final test time, T3, the virus has been completely deactivated.

Increasing the percentage of copper material to an 80% copper material 420 in the sample shown in FIG. 4 considerably decreases the amount of time that the virus remains active on the 80% copper material 420 surface. For instance, at the second test time, T2, the virus has been completely deactivated using 80% copper material 420. The second test time, T2, may correspond to a time of less than one hour (e.g., 40-45 minutes, etc.).

When the percentage of copper material in the sample surface is increased to a 90% copper material 424, the virus is completely deactivated in about 30 minutes. As the percentage of copper in a given surface material is increased from 90% to 100%, the amount of time required to completely inactivate a contacting virus is decreased. At 100% copper, the virus may be completely deactivated in the shortest amount of time (e.g., less than 30 minutes).

Figure 5:
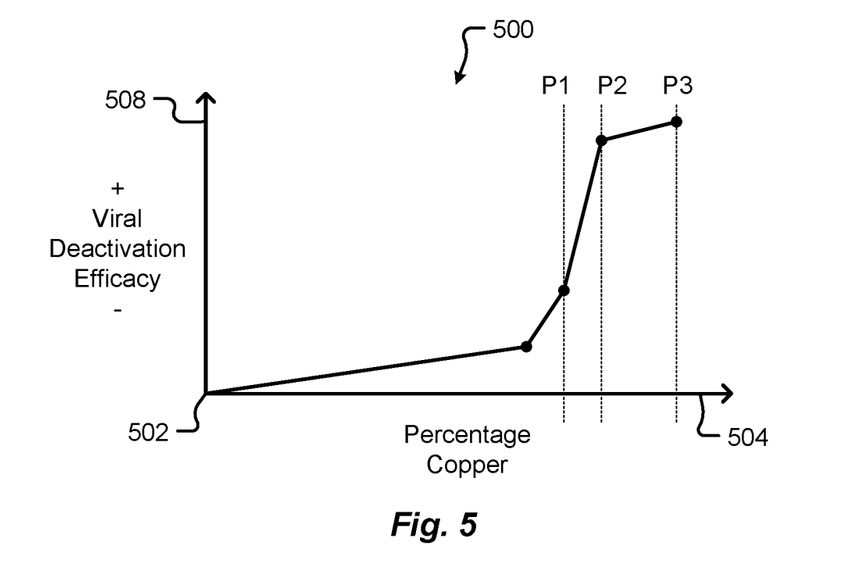
FIG. 5 shows a chart of viral deactivation efficacy for surface materials based on a percentage composition of copper.

FIG. 5 shows a chart of viral deactivation efficacy and copper percentage 500 in accordance with embodiments of the present disclosure. Based on the tests performed and described in conjunction with FIG. 4, the chart of viral deactivation efficacy and copper percentage 500 shows that as the percentage of copper making up a material in contact with a virus is increased, the efficacy of viral deactivation increases. As illustrated in FIG. 5, the chart 500 shows the percentage of copper along the horizontal axis 504 as increasing moving away from the origin 502 to the right-hand side of the chart 500. The vertical axis 508 shows the viral deactivation efficacy or the ability for a material to completely deactivate a virus in the shortest amount of time increasing moving away from the origin 502. Metal alloys containing only a fraction of an antimicrobial metal, illustrated by a portion of the curve before first percentage, P1, show a low viral deactivation efficacy. This low viral deactivation efficacy may correspond to longer amount of time that a virus remains active on a surface made from this composition of material.

As the percentage of copper is increased, moving to the right-hand side, at the first percentage, P1, the viral deactivation efficacy of the material begins to rapidly increase. The first percentage, P1, may correspond to a metal alloy containing about 70 percent copper (e.g., the 70% copper material 416 shown in the chart of surface material decay rate 400). The second percentage, P2, may correspond to a metal alloy containing about 80 percent copper (e.g., the 80% copper material 420 shown in the chart of surface material decay rate 400). At 80% copper, the viral deactivation efficacy of the material sharply increases. Between 80% copper (at the second percentage, P2) and 100% or pure copper (at the third percentage, P3), the viral deactivation efficacy of the material gradually increases to a maximum viral deactivation efficacy of the material.

Based on the charts 400, 500 of FIGS. 4 and 5, the material percentage of the antimicrobial metal plating layer 116 that achieves a high viral deactivation efficacy, reducing the amount of time that a virus remains active on a surface, may be selected from alloys containing at least 70% of the antimicrobial metal, and especially from alloys containing between 90% and 99% of the antimicrobial metal, and even more especially from a pure metal containing 100% of the antimicrobial metal. Using a copper-rich metal having a percentage greater than or equal to 90% may provide a high viral deactivation efficacy at a cost-effective price point.

Figure 6:
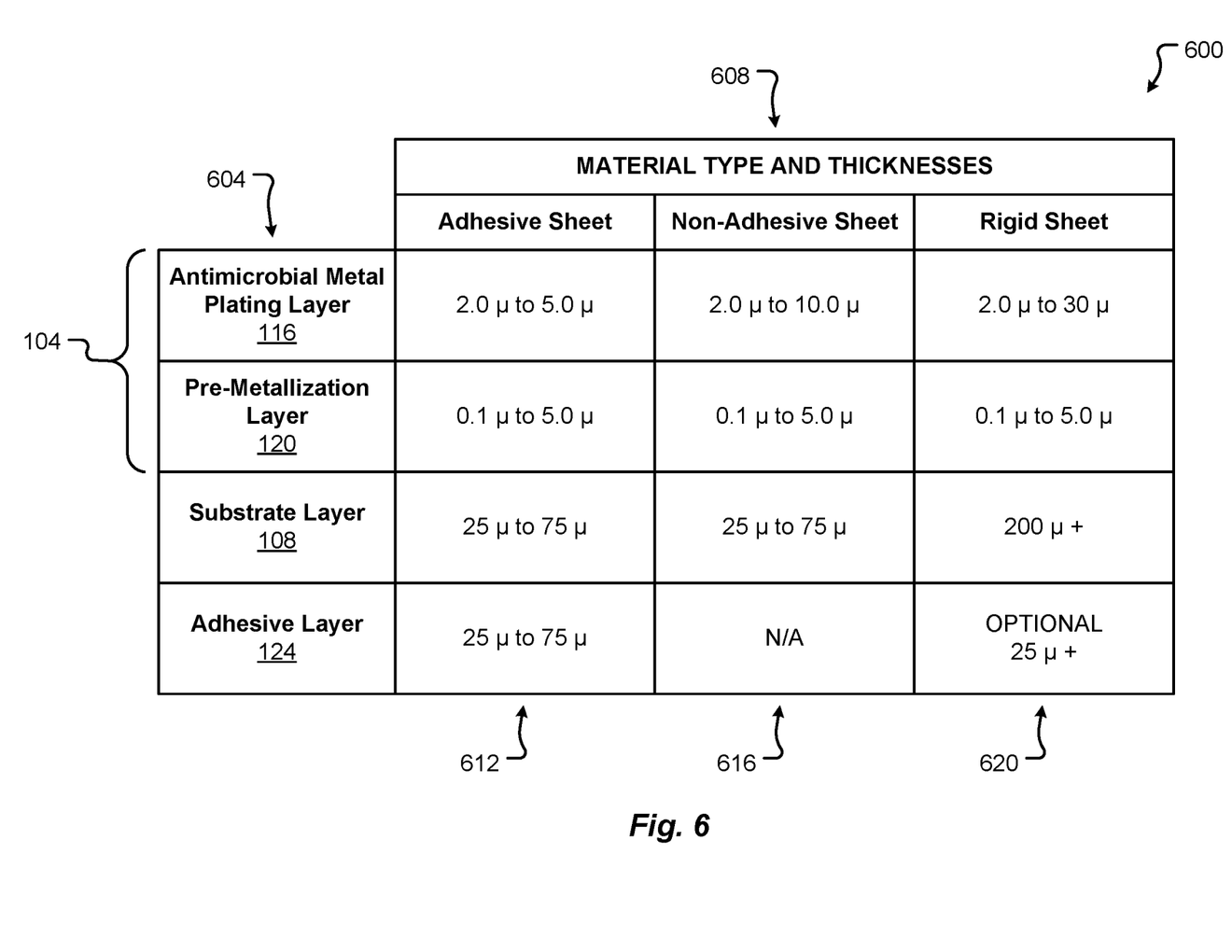
FIG. 6 shows a chart of example layer thicknesses for different material types and applications in accordance with embodiments of the present disclosure.

FIG. 6 shows a chart of layer thicknesses for material types 600 and applications in accordance with embodiments of the present disclosure. The chart 600 includes a layer identification column 604 having individual rows corresponding to the various layers making up the antimicrobial metallized thin film 100. The material type and thickness 608 columns provide example thickness ranges for each layer in the layer identification column 604. For instance, the material type and thickness 608 includes, but is in no way limited to, an adhesive sheet material type 612, a non-adhesive sheet material type 616, and a rigid sheet material type 620.

The adhesive sheet material type 612 includes at least the metallized layer 104 comprising one or more of the antimicrobial metal plating layer 116 and the pre-metallization layer 120, the substrate layer 108, and an adhesive layer 124. In some embodiments, the adhesive sheet material type 612 may include a release liner 128. The thickness of the release liner 128 may be selected from any number of dimensions. The dimensions of the antimicrobial metal plating layer 116 in the adhesive sheet material type 612 may be measured in a range from 2.0µ to 5.0µ. This size of antimicrobial metal plating layer 116 may provide enough of the antimicrobial material to deactivate a contacting virus while preventing papercuts or accidental edge cuts from antimicrobial metal plating layer 116.

The pre-metallization layer 120 for any of the sheets 612, 616, 620 may be sized in a range from 0.1µ to 5.0µ. However, it may be beneficial to limit the thickness of the pre-metallization layer 120 in a range from 0.1µ to 0.2µ to provide faster more cost-effective pre-metallization depositions. As can be appreciated, the less material deposited onto the first side 138 of the substrate layer 108 the greater the savings of time and cost.

The substrate layer 108 may be sized in a range of 25µ to 75µ for most applications and sheet types 612, 616. In some embodiments, however, an increased thickness of the substrate layer 108 may provide enhanced mechanical and/or handling properties. While the thickness of the substrate layer 108 may be sized over 75µ, in some embodiments, the thickness of the substrate layer 108 may be sized greater than 200µ. For example, the rigid sheet material type 620 may have a thicker substrate layer 108 than the other sheets 612, 616. The rigid sheet material type 620 may be deployed in high-traffic areas, onto high-impact surfaces, and/or other surfaces to be refurbished that may require greater mechanical protection.

The adhesive sheet material type 612 may include an adhesive layer 124. The non-adhesive sheet material type 616 does not include an adhesive layer 124. In some embodiments, an adhesive layer 124 may be added to the non-adhesive sheet material type 616 prior to installation or refurbishment. The rigid sheet material type 620 may optionally include the adhesive layer 124 at any thickness.

Figure 7:
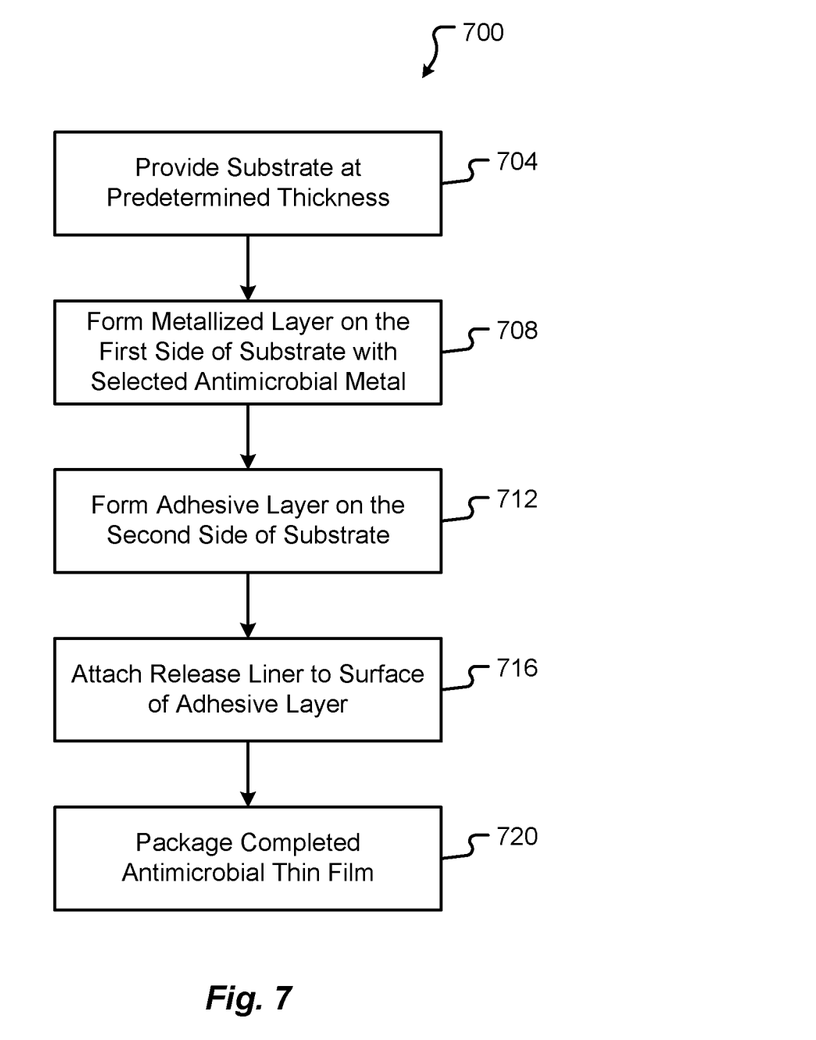
FIG. 7 is a flow diagram of a method for manufacturing an antimicrobial metallized thin film in accordance with embodiments of the present disclosure.

FIG. 7 is a flow diagram of a method 700 for manufacturing an antimicrobial metallized thin film 100 in accordance with embodiments of the present disclosure. The method 700 may be used to form any of the antimicrobial metallized thin films 100, rolls 200A, sheets 200B, 612, 616, 620, and/or plating arrangements 300A, 300B, 300C described herein. The method 700 begins by providing a substrate 108 at a predetermined thickness (step 704). The predetermined thickness may correspond to any thickness of the substrate layer 108 described in conjunction with at least FIGS. 1A-1B and 6 herein.

Next, the method 700 may continue by forming a metallized layer 104 on the first side 138 of the substrate layer 108 (step 708). The metallized layer 104 may comprise a pre-metallization layer 120 and an antimicrobial metal plating layer 116 plated to the pre-metallization layer 120. The pre-metallization layer 120 may correspond to an electroless plated or vapor-deposited layer of metal. For example, the pre-metallization layer 120 may correspond to an electroless copper plating layer, an electroless nickel plating layer, and/or some other electroless metal plating of the first side 138 of the substrate layer 108. The pre-metallization layer 120 may be a vapor-deposited copper, nickel, or some other metal plating to which the antimicrobial metal plating layer 116 may be plated (e.g., electroplated, chemically plated, etc.). The antimicrobial metal plating layer 116 may be selected from one or more antimicrobial metals. Examples of these metals may include, but are in no way limited to, copper, silver, zinc, cadmium, etc. In one embodiment, the antimicrobial metal plating layer 116 may be made from a copper-rich alloy or pure copper metal. The antimicrobial metal plating layer 116 may be formed over a majority, or even an entirety, of the first side 138 of the substrate layer 108 similar to the first plating arrangement 300A described in conjunction with FIG. 3A. In some embodiments, the antimicrobial metal plating layer 116 may be formed over discrete portions of the first side 138 of the substrate layer 108 similar to the second plating arrangement 300B and/or the third plating arrangement 300C described in conjunction with FIGS. 3B and 3C, respectively.

The method 700 may proceed by forming an adhesive layer 124 on the second side 140 of the substrate layer 108 (step 712). In one embodiment, a separate adhesive layer 124 may be attached to the second side 140 of the substrate layer 108 via pressure and/or chemical application. In some embodiments, the adhesive layer 124 may be sprayed onto the second side 140 of the substrate layer 108 and/or otherwise deposited onto the second side 140 of the substrate layer 108. The adhesive layer 124 may correspond to a double-sided adhesive tape that is adhered to the second side 140 of the substrate layer 108.

In some embodiments, the method 700 may continue by attaching a release liner 128 to the adhesive attachment surface 144 of the adhesive layer 124 (step 716). The release liner 128 may be formed or coated with at least one release agent or nonstick layer disposed on a surface thereof. The release agent, or nonstick layer, material may include, but is in no way limited to, at least one of a PET resin, polypropylene resin, polysiloxane, etc. In one embodiment, the release liner 128 may be coated with a silicone release agent that is formed on the adhesive contact surface 146 of the release liner 128. When the release liner 128 is attached to the adhesive layer 124, the adhesive contact surface 146 contacts the adhesive attachment surface 144 of the adhesive layer 124 and the silicone release agent on the adhesive contact surface 146 allows for easy separation of the release liner 128 from the adhesive attachment surface 144 of the adhesive layer 124 by, for example, peeling.

The method 700 may continue by packaging the formed antimicrobial metallized thin film 100 (step 720). The antimicrobial metallized thin film 100 may be packaged as strips, sheets (e.g., large strips), squares, and/or other shapes. These shapes may be stacked in a number of sheets of material 200B and/or wound onto cores 204 forming rolls of material 200A. Examples of packaged antimicrobial metallized thin films 100 are described at least in conjunction with FIGS. 2A and 2B.

The antimicrobial metallized thin film 100 described herein can be easily and quickly deployed onto surface to be refurbished providing a virucidal contact surface for many communal surfaces in society today. Deployment of the antimicrobial metallized thin film 100 in environments that are currently without antimicrobial surfaces can prevent the spread of disease and curb viral transmission.

References in the specification to "one embodiment," "an embodiment," "an example embodiment," "some embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in conjunction with one embodiment, it is submitted that the description of such feature, structure, or characteristic may apply to any other embodiment unless so stated and/or except as will be readily apparent to one skilled in the art from the description.

Any of the steps, functions, and operations discussed herein can be performed continuously and automatically.

While the flowchart has been discussed and illustrated in relation to a particular sequence of events, it should be appreciated that changes, additions, and omissions to this sequence can occur without materially affecting the operation of the disclosed embodiments, configuration, and aspects.

The exemplary systems and methods of this disclosure have been described in relation to antimicrobial metallized thin films and the refurbishment of communal surfaces using antimicrobial metallized thin films. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

A number of variations and modifications of the disclosure can be used. It would be possible to provide for some features of the disclosure without providing others.

The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Embodiments include an antimicrobial metallized thin film, comprising: a substrate layer having a first side and a second side disposed opposite and offset from the first side by a substrate layer thickness, the substrate layer extending planarly over a length and width of the substrate layer; a metallized layer formed on the first side of the substrate layer at a total metal thickness of less than $8.0\mu$, wherein a physical contact surface of the antimicrobial metal is exposed and uncovered along at least one of the length and width of the substrate layer; and an adhesive layer formed on the second side of the substrate layer and extending an adhesive layer thickness to an adhesive attachment surface.

Aspects of the above antimicrobial metallized thin film include wherein the metallized layer comprises an antimicrobial metal that deactivates contacting viral ribonucleic acid ("RNA"). Aspects of the above antimicrobial metallized thin film include wherein the antimicrobial metal is at least 90% copper. Aspects of the above antimicrobial metallized thin film include wherein the metallized layer completely covers the first side of the substrate layer. Aspects of the above antimicrobial metallized thin film include wherein the metallized layer comprises: a pre-metallization layer deposited on the first side of the substrate layer at a deposition thickness measured in a range from $0.05\mu$ to $0.5\mu$; and an antimicrobial metal plating layer plated onto the pre-metallization layer at a plating thickness measured in a range from $1.0\mu$ to $5.0\mu$, the antimicrobial metal plating layer comprising the physical contact surface spaced apart from the first side of the substrate layer by the deposition thickness and the plating thickness. Aspects of the above antimicrobial metallized thin film include wherein the substrate layer is a polymer film. Aspects of the above antimicrobial metallized thin film include wherein the deposition thickness is measured in a range from 0.1μ to 0.2μ, wherein the plating thickness is measured in a range from 2.0μ to 5.0μ, wherein the substrate layer is measured in a range from 25μ to 75μ, and wherein the polymer film is a nonconductive material. Aspects of the above antimicrobial metallized thin film further comprise: wherein the pre-metallization layer is printed onto the first side of the substrate layer via at least one of a silver, a copper, and a graphite metallic printing ink. Aspects of the above antimicrobial metallized thin film include wherein the antimicrobial metallized thin film is wound in a roll onto a core. Aspects of the above antimicrobial metallized thin film include wherein the adhesive layer comprises at least one of a pressure-sensitive adhesive material, a solvent-based adhesive material, and a thermoplastic adhesive material. Aspects of the above antimicrobial metallized thin film further comprise: a release liner attached to the adhesive attachment surface, wherein the release liner is coated with a nonstick layer of silicone on an adhesive contact surface of the release liner. Aspects of the above antimicrobial metallized thin film include wherein the antimicrobial metal is brass comprising 90% copper and 10% zinc. Aspects of the above antimicrobial metallized thin film include wherein the antimicrobial metal is brass comprising 95% copper and 5% zinc.

Embodiments include an antimicrobial metallized substrate, comprising: a polymer film having a first surface and a second surface disposed opposite the first surface, the first surface offset from the second surface by a film thickness, the polymer film providing a metallization area on the first surface; a pre-metallization material layer comprising a conductive metal deposited on the metallization area of the first surface; a metal layer comprising at least 90% copper plated onto the pre-metallization material layer at a metal thickness measured in a range from 2.0μ to 5.0 microns, wherein the metal layer comprises an exposed contact surface that is uncovered along a complete length of the polymer film; and an adhesive layer formed on the second surface of the substrate layer and extending an adhesive layer thickness to an adhesive attachment surface.

Aspects of the above antimicrobial metallized substrate include wherein the pre-metallization layer is printed onto the first side of the substrate layer via at least one of a silver, a copper, and a graphite metallic printing ink. Aspects of the above antimicrobial metallized substrate include wherein the metal layer deactivates contacting viral ribonucleic acid ("RNA"). Aspects of the above antimicrobial metallized substrate include wherein the metal layer is brass comprising 95% copper and 5% zinc. Aspects of the above antimicrobial metallized substrate include wherein the pre-metallization material layer is vapor-deposited on metallization area of the first surface at a deposition thickness measured in a range from 0.1μ to 0.2μ, and wherein the film thickness is measured in a range from 25μ to 75μ. Aspects of the above antimicrobial metallized substrate include wherein the film thickness is at least 200μ, and wherein the antimicrobial metallized substrate is shaped as a laminate sheet having a total length and a total width.

Embodiments include a method of refurbishing a communal surface of an object by attaching an antimicrobial metallized thin film to the surface, comprising: providing the antimicrobial metallized thin film, comprising: a substrate layer having a first side and a second side disposed opposite and offset from the first side by a substrate layer thickness, the substrate layer extending planarly over a length and width of the substrate layer; a pre-metallization layer of metal deposited onto the first side of the substrate layer at a deposition thickness; and an antimicrobial metal plating layer plated onto the pre-metallization layer at a plating thickness, wherein the antimicrobial metal plating layer comprises an antimicrobial metal selected from at least one of copper, silver, zinc, and cadmium, and wherein a physical contact surface of the antimicrobial metal is uncovered along at least one of the length and width of the substrate layer; and selecting the communal surface of the object to be refurbished with the antimicrobial metallized thin film; and attaching the second side of the substrate layer to the communal surface of the object to be refurbished causing the antimicrobial metallized thin film to remain on the communal surface of the object such that the antimicrobial metal is exposed to physical contact.

Aspects of the above method include wherein the antimicrobial metal deactivates contacting viral ribonucleic acid ("RNA"). Aspects of the above method include wherein prior to attaching the second side of the substrate layer to the communal surface of the object to be refurbished, the method further comprises: applying an adhesive material to the communal surface of the object to be refurbished; cutting the antimicrobial metallized thin film to a size of the communal surface of the object to be refurbished; and adhering at least a portion of the second side of the substrate layer to the adhesive material applied to the communal surface of the object to be refurbished. Aspects of the above method include wherein the pre-metallization layer is printed onto the first side of the substrate layer via at least one of a silver, a copper, and a graphite metallic printing ink. Aspects of the above method include wherein an adhesive layer is formed on the second side of the substrate layer extending an adhesive layer thickness. Aspects of the above method include wherein prior to applying the adhesive material to the communal surface of the object to be refurbished, the method further comprises: separating at least a portion of a release liner attached to the adhesive attachment surface exposing the adhesive attachment surface. Aspects of the above method include wherein the antimicrobial metallized thin film further comprises: a preformed adhesive layer attached to the second side of the substrate layer. Aspects of the above method include wherein the antimicrobial metallized thin film further comprises: a release layer attached to an adhesive side of the preformed adhesive layer. Aspects of the above method include wherein attaching the second side of substrate layer to the communal surface of the object to be refurbished comprises adhering an exposed adhesive side of preformed adhesive layer to the object to be refurbished. Aspects of the above method include wherein the second side of the substrate layer is attached to the communal surface of the object to be refurbished without at least one of shaping the antimicrobial metallized thin film, sizing the antimicrobial metallized thin film, cutting the antimicrobial metallized thin film, and adding any intermediate layer between the preformed adhesive layer and the communal surface of the object to be refurbished.

Any one or more of the aspects/embodiments as substantially disclosed herein.

Any one or more of the aspects/embodiments as substantially disclosed herein optionally in combination with any one or more other aspects/embodiments as substantially disclosed herein.

One or means adapted to perform any one or more of the above aspects/embodiments as substantially disclosed herein.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

The terms "determine," "calculate," "compute," and variations thereof, as used herein, are used interchangeably and include any type of methodology, process, mathematical operation or technique.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

What is claimed is:

1. An antimicrobial metallized thin film, comprising:
   a substrate layer having a first side surface and a second side surface disposed opposite and offset from the first side surface by a substrate layer thickness, the substrate layer comprising a length and a width;
   a metallized layer formed onto the first side surface of the substrate layer, the metallized layer comprising an antimicrobial metal, wherein a physical contact surface of the antimicrobial metal is exposed and uncovered along at least one of the length and the width, and wherein the metallized layer is formed onto the first side surface of the substrate layer as a plurality of discontinuous regions separated apart from one another by a separation distance, the separation distance exposing uncovered portions of the substrate layer between the plurality of discontinuous regions, and wherein the metallized layer comprises:
      a pre-metallization layer deposited onto the first side surface of the substrate layer at a deposition thickness measured in a range from 0.05 µm to 0.5 µm; and
      an antimicrobial metal plating layer plated onto the pre-metallization layer at a plating thickness measured in a range from 1.0 µm to 5.0 µm, the antimicrobial metal plating layer comprising the physical contact surface spaced apart from the first side surface of the substrate layer by the deposition thickness and the plating thickness; and
   an adhesive layer formed onto the second side surface of the substrate layer and extending an adhesive layer thickness to an adhesive attachment surface of the adhesive layer.

2. The antimicrobial metallized thin film of claim 1, wherein the separation distance is measured in a range from 3 µm to 120 µm.

3. The antimicrobial metallized thin film of claim 1, wherein the antimicrobial metal is at least 90% copper.

4. The antimicrobial metallized thin film of claim 1, wherein the antimicrobial metallized thin film is wound in a roll onto a core.

5. The antimicrobial metallized thin film of claim 1, wherein the antimicrobial metal is brass comprising 90% copper and 10% zinc.

6. The antimicrobial metallized thin film of claim 1, wherein the antimicrobial metal is brass comprising 95% copper and 5% zinc.

7. The antimicrobial metallized thin film of claim 1,
   wherein the deposition thickness is measured in a range from 0.1 µm to 0.2 µm, wherein the plating thickness is measured in a range from 2.0 µm to 5.0 µm, wherein the substrate layer is measured in a range from 25 µm to 75 µm, and wherein the substrate layer is a nonconductive polymer material.

8. The antimicrobial metallized thin film of claim 7, wherein the pre-metallization layer is printed onto the first side surface of the substrate layer via at least one of a silver metallic printing ink, a copper metallic printing ink, and a graphite ink.

9. The antimicrobial metallized thin film of claim 7, wherein the adhesive layer comprises at least one of a pressure-sensitive adhesive material, a solvent-based adhesive material, and a thermoplastic adhesive material.

10. The antimicrobial metallized thin film of claim 9, further comprising:
    a release liner attached to the adhesive attachment surface, wherein the release liner is coated with a nonstick layer of silicone on an adhesive contact surface of the release liner.

11. An antimicrobial metallized substrate, comprising:
    a polymer film having a first surface and a second surface disposed opposite the first surface, the first surface offset from the second surface by a film thickness, the polymer film providing a metallization area on the first surface;
    a pre-metallization material layer comprising a conductive metal deposited on the metallization area of the first surface;
    a metal layer comprising at least 90% copper plated onto the pre-metallization material layer, wherein the metal layer comprises an exposed contact surface that is uncovered along a complete length of the polymer film, and wherein the metal layer is formed onto the first surface of the pre-metallization material layer as a plurality of discontinuous regions separated apart from one another by a separation distance, the separation distance exposing uncovered portions of the polymer film between the plurality of discontinuous regions; and
    an adhesive layer formed on the second surface of the polymer film and extending an adhesive layer thickness to an adhesive attachment surface.

12. The antimicrobial metallized substrate of claim 11, wherein the separation distance is measured in a range from 3 µm to 120 µm.

13. The antimicrobial metallized substrate of claim 11, wherein the pre-metallization material layer is printed onto the first surface of the polymer film via at least one of a silver metallic printing ink, a copper metallic printing ink, and a graphite ink.

14. The antimicrobial metallized substrate of claim 11, wherein the metal layer is brass comprising 95% copper and 5% zinc.

15. The antimicrobial metallized substrate of claim 11, wherein the pre-metallization material layer is vapor-deposited on the metallization area of the first surface at a deposition thickness measured in a range from 0.1 µm to 0.2 µm, and wherein the film thickness is measured in a range from 25 µm to 75 µm.

16. The antimicrobial metallized substrate of claim 11, wherein the film thickness is at least 200 µm, and wherein the antimicrobial metallized substrate is shaped as a laminate sheet having a total length and a total width.

17. The antimicrobial metallized substrate of claim 11, wherein the pre-metallization material layer comprises a plurality of discontinuous pre-metallization regions that are separated apart from one another by the separation distance.

18. An antimicrobial metallized thin film, comprising:
a substrate layer having a first side surface and a second side surface disposed opposite and offset from the first side surface by a substrate layer thickness, the substrate layer comprising a length and a width; and
a metallized layer formed onto the first side surface of the substrate layer, the metallized layer comprising an antimicrobial metal, wherein a physical contact surface of the antimicrobial metal is exposed and uncovered along at least one of the length and the width, and wherein the metallized layer is formed onto the first side surface of the substrate layer as a plurality of discontinuous regions separated apart from one another by a separation distance, the separation distance exposing uncovered portions of the substrate layer between the plurality of discontinuous regions, and wherein the metallized layer comprises:
a pre-metallization layer deposited onto the first side surface of the substrate layer at a deposition thickness measured in a range from 0.05 µm to 0.5 µm; and
an antimicrobial metal plating layer plated onto the pre-metallization layer at a plating thickness measured in a range from 1.0 µm to 5.0 µm, the antimicrobial metal plating layer comprising the physical contact surface spaced apart from the first side surface of the substrate layer by the deposition thickness and the plating thickness.

19. The antimicrobial metallized thin film of claim 18, wherein the separation distance is measured in a range from 3 µm to 120 µm.

20. The antimicrobial metallized thin film of claim 18, wherein the pre-metallization layer is printed onto the first side surface of the substrate layer via at least one of a silver metallic printing ink, a copper metallic printing ink, and a graphite ink.

* * * * *